United States Patent

Nonaka et al.

Patent Number: 6,080,992
Date of Patent: Jun. 27, 2000

[54] APPARATUS FOR FIXING RADIATION BEAM IRRADIATION FIELD FORMING MEMBER

[75] Inventors: Hideki Nonaka; Nobutaka Manabe, both of Niihama, Japan

[73] Assignee: Sumitomo Heavy Industries, Ltd., Tokyo, Japan

[21] Appl. No.: 09/129,838

[22] Filed: Aug. 6, 1998

[30] Foreign Application Priority Data

Aug. 7, 1997 [JP] Japan ................................. 9-213240

[51] Int. Cl.$^7$ ........................................ G21K 1/02
[52] U.S. Cl. .............................. 250/505.1; 250/492.3; 378/147
[58] Field of Search ........................... 250/492.3, 505.1; 378/147

[56] References Cited

U.S. PATENT DOCUMENTS

| | | | |
|---|---|---|---|
| 3,114,043 | 12/1963 | Thomas et al. | 378/147 |
| 4,140,129 | 2/1979 | Heinz et al. | 250/505.1 |
| 4,221,971 | 9/1980 | Burger | 250/505.1 |
| 5,866,914 | 2/1999 | Jones | 250/505.1 |

FOREIGN PATENT DOCUMENTS 0 417 964   3/1991   European Pat. Off. .

Primary Examiner—Jack Berman
Attorney, Agent, or Firm—Arent Fox Kintner Plotkin & Kahn, PLLC

[57] ABSTRACT

A bolus and final collimators are inserted into an apparatus for fixing radiation beam irradiation field forming member, fixed on the front end of radiation beam irradiating section within a rotation gantry, through grooves of a frame, and pushed in by a door until they reach a specified position determined by the existence of a back panel. Through this arrangement it is possible to easily perform an exchange of boluses and final collimators which is required each time therapy is renewed for a patient, and to accurately determine the position of new bolus and final collimators.

16 Claims, 12 Drawing Sheets

6,080,992

APPARATUS FOR FIXING RADIATION BEAM IRRADIATION FIELD FORMING MEMBER

BACKGROUND OF THE INVENTION

1. Field of the Invention

This invention relates to an apparatus for fixing a radiation beam irradiation field forming member to form the irradiation field matching with the shape of an object to be irradiated, to the end of irradiating section of a rotating radiation chamber (to be referred to as gantry). The apparatus for fixing the radiation beam irradiation field forming member comprises a bolus and a final collimator: the former, while radiation beams are being irradiated within the gantry, adjusts shape of cross-section of the irradiation field at the largest depth; and the latter finally determines shape of the irradiation field. This invention relates particularly to an apparatus for fixing a radiation beam irradiation field forming member which is preferably used for fixing the radiation beam irradiation field forming member at the end of irradiating section which rotates round a patient when a proton beam is irradiated for the treatment of cancer.

2. Description of the Prior Art

Conventional cancer therapy based on radiation of active rays uses X-rays, gamma rays, electron beams, fast neutron beams, etc. These active rays, as shown in FIG. 12, become the strongest at sites close to the surface of a patient, and thus may inflict damages on normal tissues close to the body surface when those rays are directed towards a cancer in a deeper part of the body. By the way, a proton or a particle which comes into being when a hydrogen atom has been removed of the electron, has a positive charge, and has a mass 1836 times as large as that of electron, can be accelerated under a high energy state by an accelerator to give a proton beam. The proton-beam is characterized by having the maximum dose peak or a Bragg peak P at a certain depth from the body surface, and then declining rapidly to zero.

This is because, as the electric force a proton exerts on electrons becomes large in proportion to its proximity to the latter, when the proton has a high kinetic energy and runs at a high speed, the time for the proton to interact with nearby electrons is short, and ionization is small in magnitude, but, when it loses the kinetic energy to nearly make a stop, the time for interaction becomes long and ionization rapidly increases in magnitude.

Thanks to this nature peculiar to protons, it is possible to apply proton beams for cancer therapy keeping normal cells other than a cancer comparatively free from damages, even if the cancer lies in a deeper part of the body. Further, as the radiation-based biological effect (RBE) of a proton beam is nearly equal to that of X-rays, the proton radiation therapy is advantageous in that it can make the most of knowledge and experience accumulated in the field of conventional X-ray radiation therapy. With these features, the proton radiation therapy device is being introduced as a therapy means to treat a cancer without removing any functional organs and encroaching on the quality of life.

In the radiation therapy of cancer, it is ideal to concentrate a lethal dose of active rays onto the cancer alone without inflicting any irreversible damages to nearby normal tissues. The Proton radiation therapy, as shown in FIG. 12, exploits the feature characteristic with protons that a proton beam incident on a substance gives the maximum dose or Bragg peak P just before it ceases to move. Namely the therapy in question aims at achieving this ideal by covering only the cancerous lesion with that Bragg peak.

By the way, protons obtained from an accelerator are in the form of a slender beam, and its energy is constant (the depth of Bragg peak is also constant). On the other hand, cancerous lesions are varied in size and have complex shapes, and their depths in the body are not constant. Further, the density of tissues through which a proton beam must pass is not constant neither. Accordingly, to achieve an effective radiation therapy, it is necessary to (1) enlarge the proton beam to have a sufficient width to cover the whole cancer lesion in one radiation; (2) adjust the beam energy according to the depth of lesion; (3) give a sufficient energy distribution in depth so that the whole cancer lesion having a certain depth can receive a uniform irradiation; and (4) make corrections according to the irregularities in contour of the lesion, and in density of the tissues through which the proton beam must pass.

To meet these requirements, a device as shown in FIG. 13 is introduced whereby an irradiation field is formed in accordance with the shape of a lesion to be radiated. To put it more specifically, a slender proton beam 20 transmitted to an irradiating section is passed through a scattering body 22 made of lead with a thickness of several millimeters to be converted into a wide beam 24 extending crosswise. Out of the wide beam 24 which widens in a conical form with the summit at the scattering body 22, picked up by a collimator described below is a portion which is close to the central axis and comparatively uniform in dose distribution. This beam gives an irradiation field of about ten and several centimeters in diameter necessary for therapy on a therapeutic platform below (not illustrated here).

The widened beam 24 is incident on a fine degrader 26 which adjusts the maximum attainable depth in accordance with the depth of a lesion to be treated (for example, a tumor 12 in the patient's body 10). The fine degrader 26 is composed, for example, of two wedge-shaped acryl blocks 26a and 26b placed opposite to each other, and adjustment of overlaps of the two blocks 26a and 26b enables a continuous alteration of the thickness through which the proton beam must pass. The proton beam loses energy in accordance with the thickness through which it must pass, and thus the depth it can reach varies in accordance therewith. Thus, adjustment by means of this fine degrader 26 makes it possible for Bragg peak P shown in FIG. 12 to fall at the same depth at which the lesion requiring therapy lies.

The proton beam, after having passed the fine degrader 26, is incident on a ridge filter 28 which is introduced to confer an energy depth distribution ΔP to the proton beam in accordance with the thickness of tumor 12. The ridge filter 28 consists of metal rods placed in parallel like a series of steps which have different thickness with each other. Proton beams passing through the metal rods different in thickness have Bragg peaks P at different depths. Thus, expansion of the range of peaks or ΔP can be achieved by adjusting the width and height of those "steps" to give appropriate overlaps.

The proton beam, after having passed through the ridge filter 28, is incident on a block collimator 30 which roughly adjusts the planar form of proton beam. The reason why the block collimator 30 is introduced here for the adjustment of beam shape, in addition to a final collimator described later, is to prevent secondary radiation due to the block collimator from occurring close to the patient's body.

The proton beam, after having passed through the block collimator 30, is incident on a bolus 32 or a resin-made irregularly formed filter, for example, and receives corrections in accordance with the cross-sectional shape of tumor 12 at the maximum depth, and the irregularities of involved tissues. The shape of bolus 32 is determined on the basis of the electron densities of nearby tissues determined from the contour line of tumor 12 and, for example, X-ray CT data of that tumor.

The proton beam, after having passed through the bolus 32, is incident on a final collimator 34 made of brass, for example, receives a final correction in accordance with the contour of planar shape of the tumor 12, and strikes the patient 10 as a therapeutic proton beam 36.

As the conventional proton radiation therapy device has been used for experimental purposes, and its whole device including the irradiating section is fixed, the bolus 32 and the final collimator 34 are simply placed on a table, or fixed with simple fixing devices. Then, their alignment is adjusted each time the experiment is renewed.

However, when a radiation therapy device is used for actual clinical applications, it is likely to be used at a frequency of once every 20 minutes, and hence it is necessary to properly place and fix the bolus 32 and the final collimator 34 quickly. Further, as the device is handled by a physician or a radiological technician instead of an engineer, it should be so designed that it does not require any special technique, and its handling must be easy. Further, with a device currently designed by the inventors (not yet publicly disclosed), as shown in FIG. 1, an irradiating section 120 of a proton beam 36 after adjustment of the shape of radiation, is mounted to a rotation gantry 100 which can rotate round a treatment bed 200 upon which a patient is fixed. In this case, during use, the radiation beam irradiating section is rotated 360° round the patient, and thus, it is necessary to fix the bolus and the final collimator so firmly for fear that they may fall by gravitation.

SUMMARY OF THE INVENTION

This invention aims at providing an apparatus for fixing a radiation beam irradiation field forming member within a gantry which satisfies above requirements and is suitably applied to a proton radiation therapy device for medical use.

This invention achieves above object by providing an apparatus for fixing a radiation beam irradiation field forming member to form an irradiation field matching with a shape of an object to be irradiated, when radiation beams are irradiated in a gantry, which fixes, to the end of radiation beam irradiating section within the gantry, the irradiation field forming member which comprises a bolus and a final collimator, of which the former adjusts a shape of cross-section of the irradiation field at the largest depth, and the latter finally determines a shape of the irradiation field, and by providing the apparatus with a frame fixed on the end of radiation beam irradiating section and having on both sides grooves through which the bolus and the final collimator to be inserted from front; a door through which the bolus and the final collimator which have been inserted into the frame are pushed from front up to a specified position; and a member which places the bolus and the final collimator thus pushed by way of the door into a proper position at the rear part of the frame.

Further, the grooves at both sides of said frame may be made to have asymmetrical cross-sections, so that the bolus and the final collimator can not be inserted thereinto in the reverse manner.

Furthermore, the final collimator may be divided into plural segments in the radiation direction of radiation beam so that they are arranged in a laminated structure in the frame during use. This arrangement makes the final collimator made of a heavy metal such as brass easy to handle.

Still further, a pusher may be provided on the inside of said door to ensure a complete pushing of the bolus and the final collimator during closure of the door. This mechanism ensures the bolus and the final collimator to be perfectly pushed into a specified position, when the door is shut.

Still further, a limit switch may be provided close to the rear end of inner surface of the frame, which detects the complete insertion of the bolus and the final collimator into the frame. This mechanism is provided to electrically check the complete insertion of the bolus and the final collimator into the frame.

Still further, a touch sensor may be provided on the front end of the frame, so that, when the touch sensor is activated, movement of the radiation beam irradiating section is arrested. This mechanism is provided to ensure safety when the irradiating section touches a man or an object by accident.

In addition, an adapter may be provided to allow smaller bolus and final collimator which are used for a case where a small irradiation field is required, to be inserted into the same frame. This mechanism allows the bolus and the final collimator to be prepared small to adapt to a case where a small irradiation field is required. This makes the storage and handling of the bolus and the final collimator far easier than is otherwise possible.

According to this invention, accurate positioning of the bolus and the final collimator within the gantry which is required each time patients are exchanged for examination, can be carried out quickly and easily. Accordingly, this invention is greatly helpful for promoting the practicality of a proton radiation therapy device for cancer, which has been still at an experimental stage.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Figure 1:
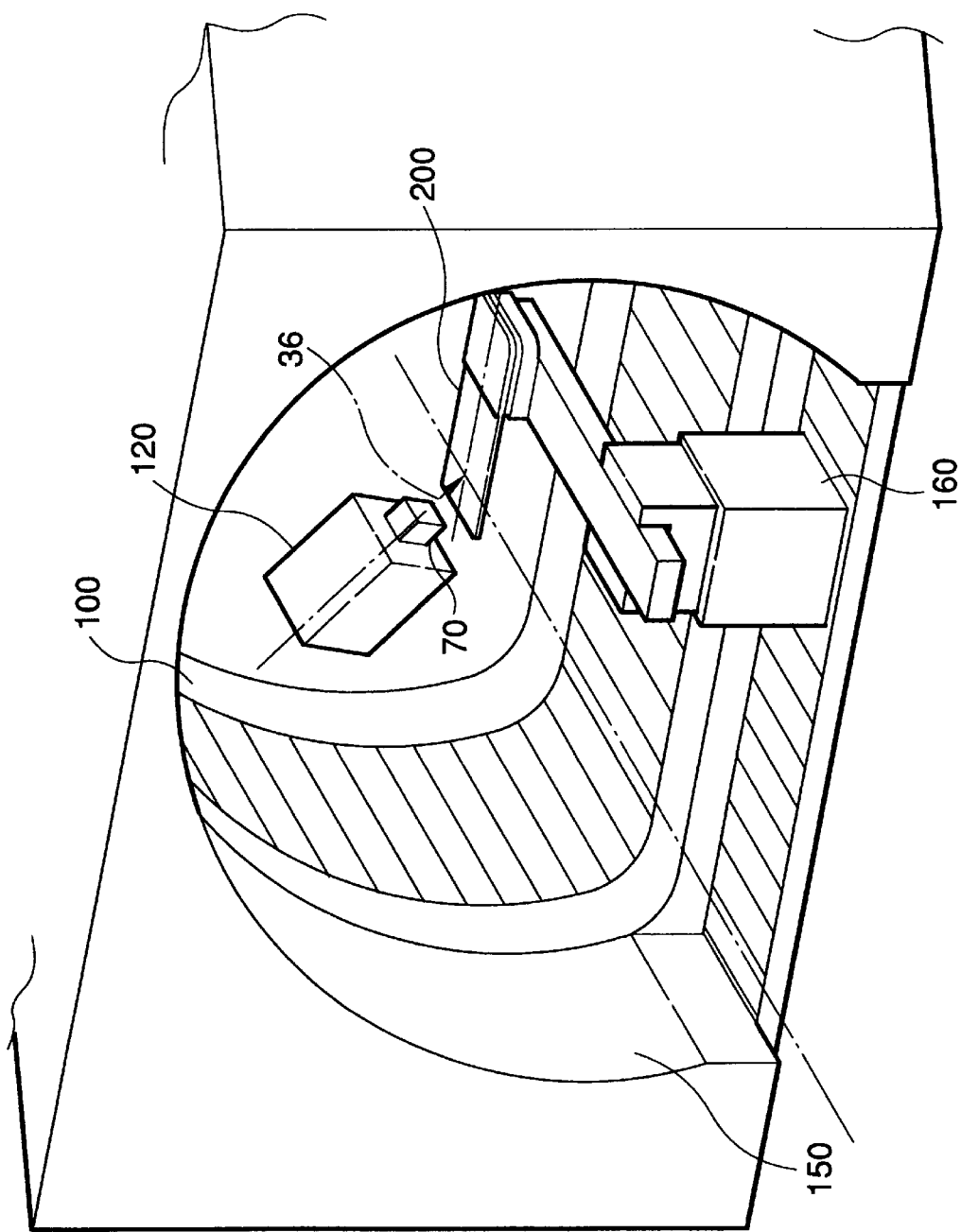
FIG. 1 is a perspective view illustrating how the radiation beam irradiating section to which the apparatus for fixing the irradiation field forming member of this invention has been mounted is attached to a rotation gantry.

The embodiments of this invention will be described in detail below with reference to the figures, where, as shown in FIG. 1, a radiating section 120 of a proton beam 36 is installed in a proton radiation therapy device which has a rotation gantry 100 rotatable round a treatment bed 200.

In FIG. 1, 150 stands for a preparation room prepared in front of the rotation gantry 100; and 160 for a bed driving mechanism to move, from the preparation room 150, the bed 200 into the rotation gantry 100 along six axes (x, y and z, and θx, θy and θz) freely.

Figure 2:
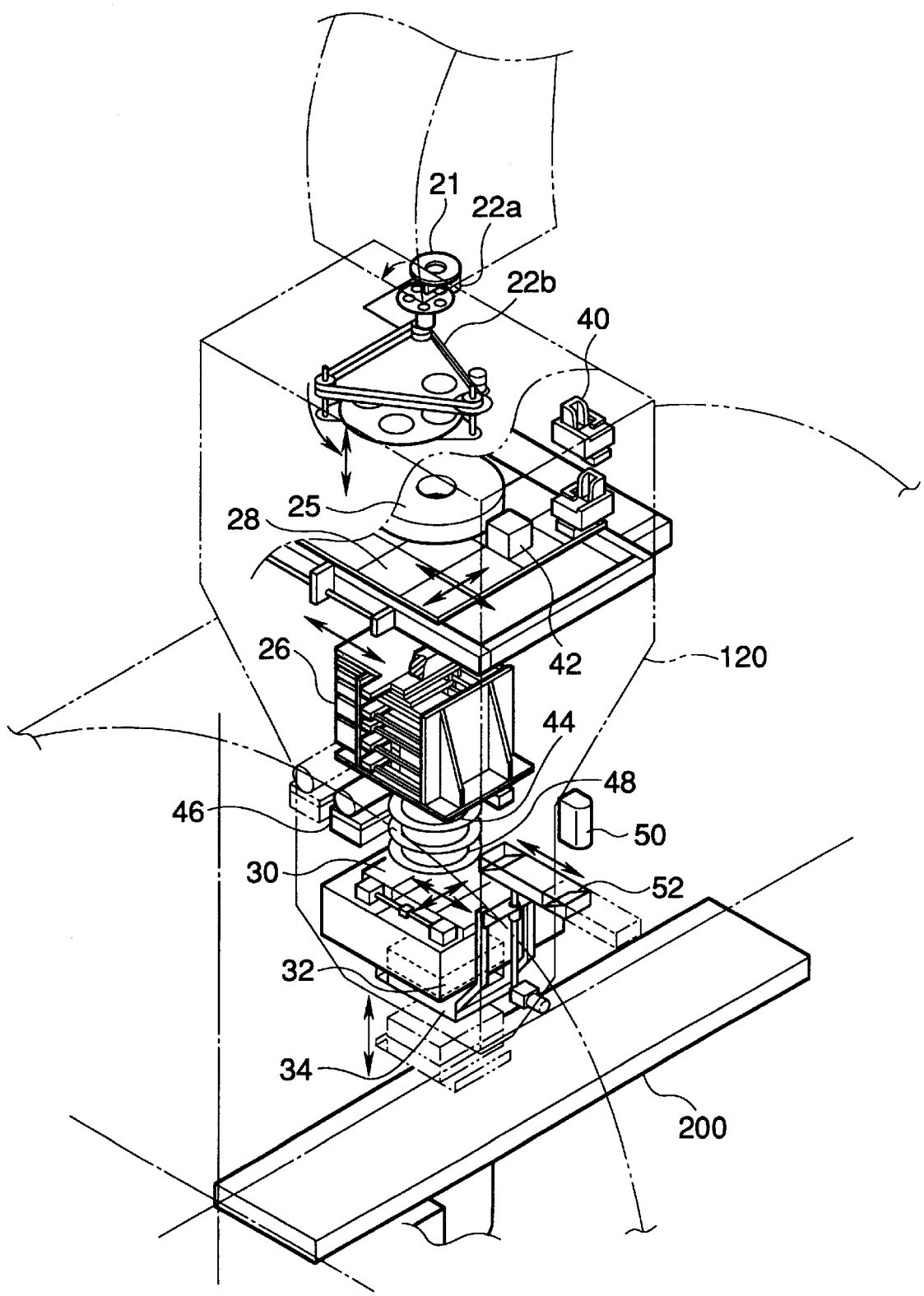
FIG. 2 is a similar perspective view illustrating the internal structure of the radiation beam irradiating section.

The overall composition of the radiation beam irradiating section 120 of this embodiment is as shown in FIG. 2. In FIG. 2, 21 stands for a profile monitor; 22a and 22b for first and second scattering bodies; 25 for a ring collimator; 26 for a fine degrader; 28 for a ridge filter; 30 for a block collimator; 32 for a bolus; 34 for a final collimator; 40 for a wobbler electromagnet; 42 for a projector; 44 for a dose monitor; 46 for an X-ray tube for monitoring; 48 for a flatness monitor for dose; 50 for a laser pointer which is used when the radiation position is adjusted with respect to the patient's body; and 52 for a mirror unit to change the direction of a laser beam projected from the laser pointer 50.

The apparatus 70 for fixing the irradiation field forming member of the first embodiment of this invention, as shown in FIGS. 3 to 6, comprises a frame 72 having grooves 73a and 73b on both sides to receive from front the final collimator which has been divided into three segments, 34a, 34b and 34c (see FIG. 7) along the radiation direction of a proton beam (along the vertical direction in FIGS. 3 to 5); a door 74 by which one can push, from front, the bolus 32 and the final collimators 34a, 34b and 34c which have been inserted into the frame 72, until they are properly put into a specified position; and a back panel 76 to receive the thus pushed bolus and final collimator, and the apparatus is fixed at the front end (the part at the lowest end in FIGS. 3–6) of the radiation beam radiating section 120.

The grooves 73a, 73b provided on both sides of said frame 72 are asymmetrical in shape when viewed from the side of door, so that, insertion of the bolus 32 and the final collimators 34a, 34b and 34c thereinto in the reverse manner never takes place.

Figure 7:
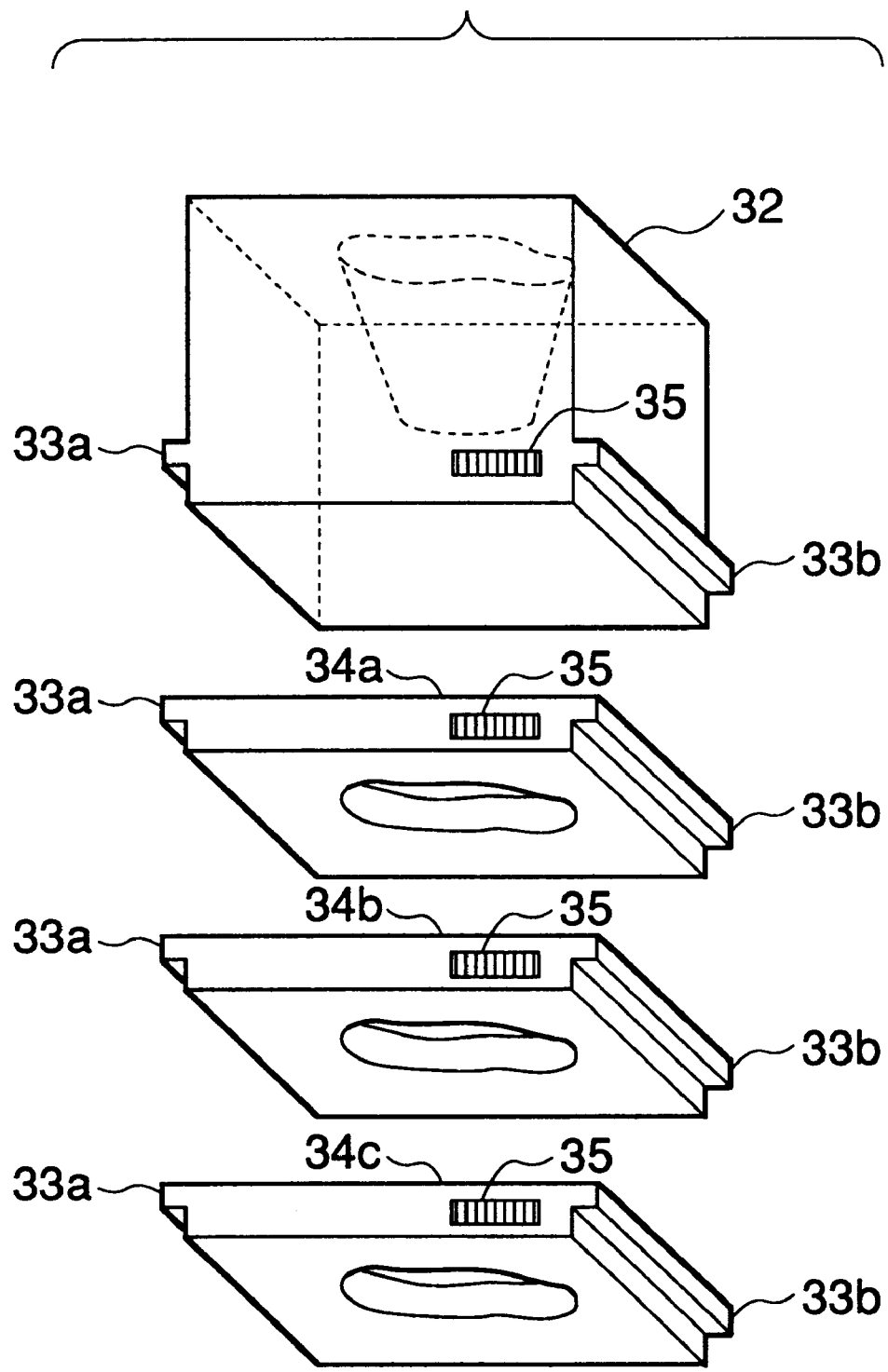
FIG. 7 is a disintegrated, perspective view illustrating how the bolus and the final collimator are layered one over another.

The bolus 32 and the final collimators 34a, 34b and 34c has, on both of their lateral sides, as shown in FIG. 7, projected lines 33a and 33b to engage with the grooves 73a and 73b.

Figure 3:
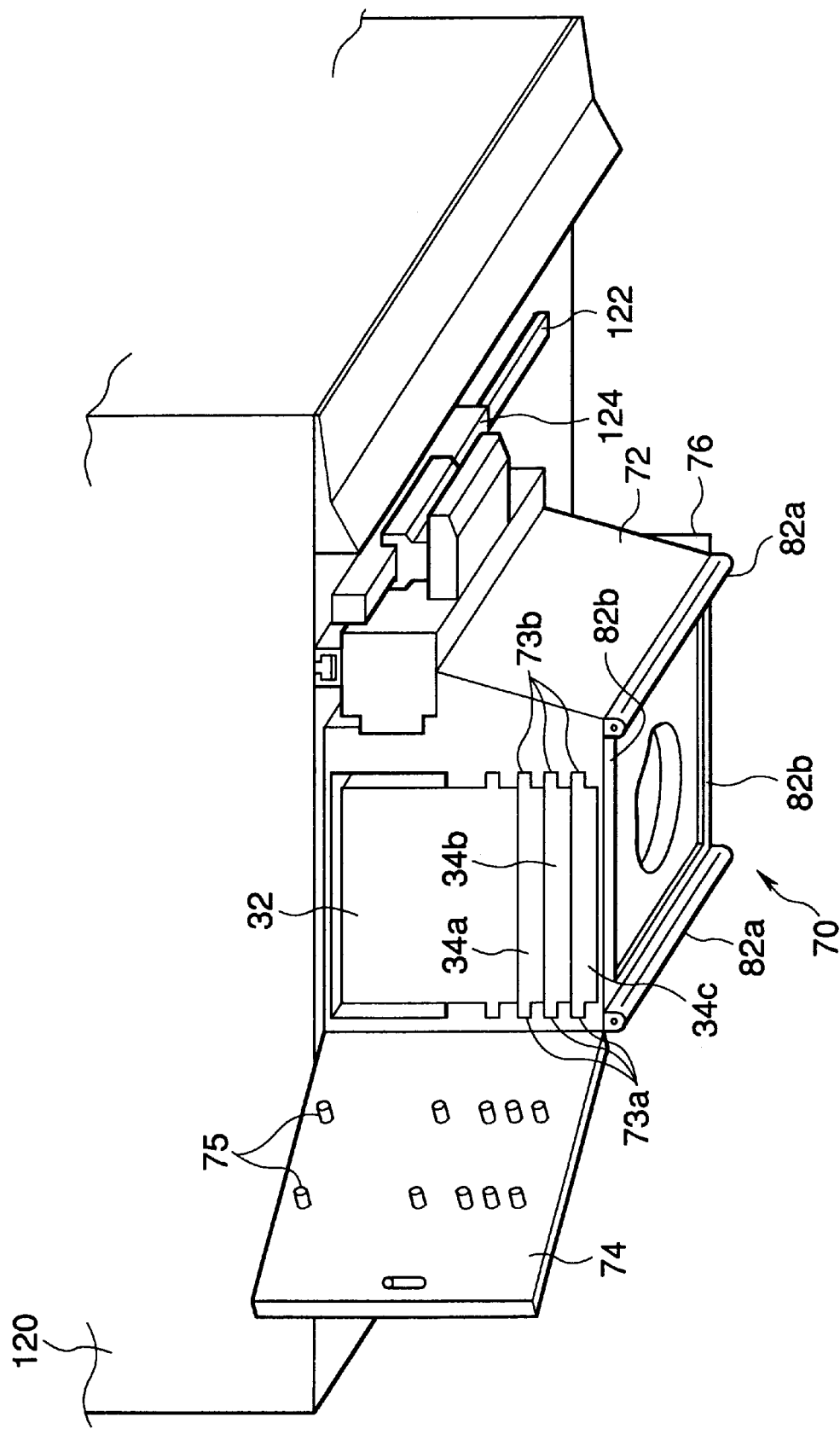
FIG. 3 is a perspective view illustrating how the first embodiment of this invention is drawn forward towards front end of the radiation beam irradiating section to exchange the irradiation field forming members, with its door opened.
Figure 4:
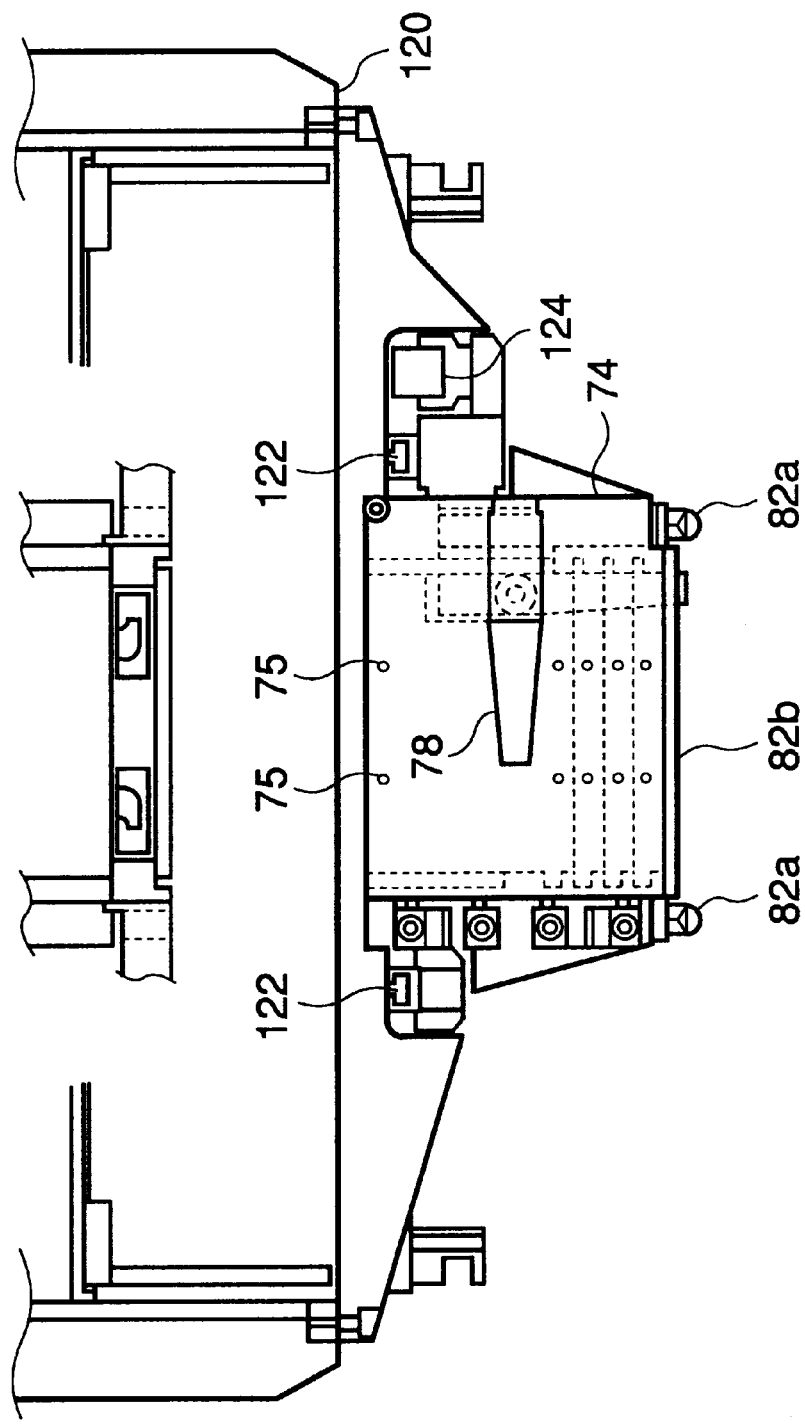
FIG. 4 is a front view of the first embodiment with its door closed.
Figure 5:
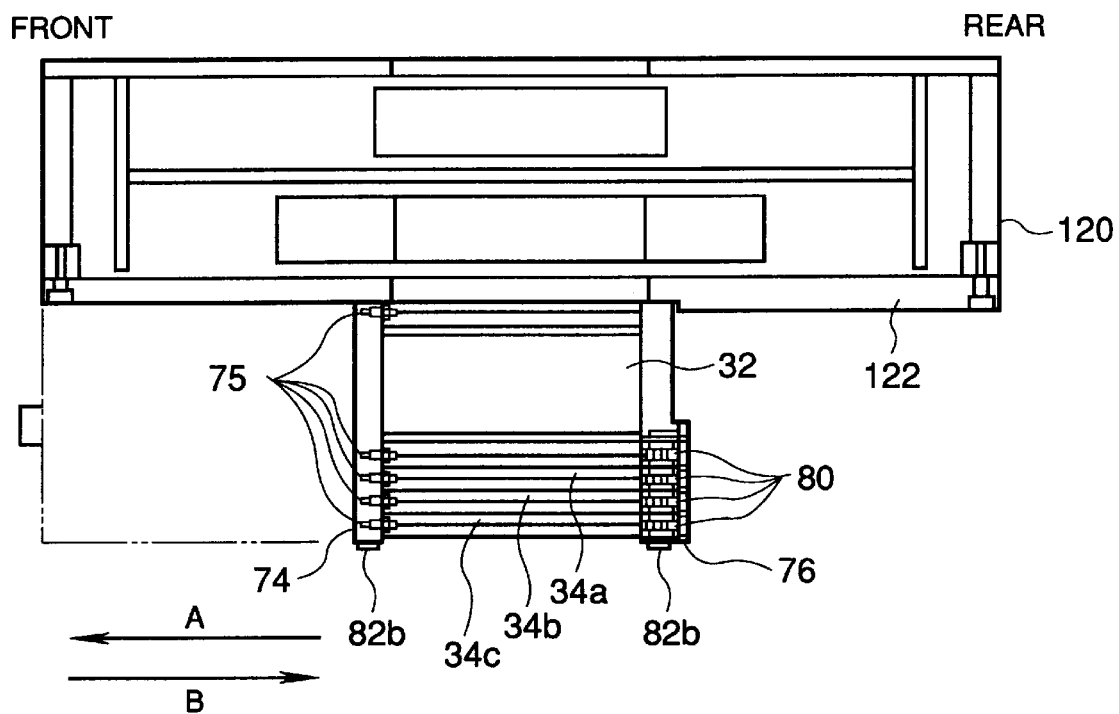
FIG. 5 is a cross-sectional view, viewed from the right side, illustrating how the same embodiment is pushed to a proton beam irradiation position.

The final collimator is divided, as shown in FIG. 7, into three segments along the radiation direction of the proton beam (vertical direction in the figure), and, as shown in FIGS. 3 to 5, is so constructed as to be laminated in the frame 72 during use. This makes easier the transportation of the final collimator usually made of a metal such as brass, or its insertion into the frame 72 than is otherwise possible.

Bar codes 35 are pasted on the bolus 32 and the final collimators 34a, 34b and 34c, so that it is possible to easily check in advance whether a given combination is appropriate for the treatment of a patient.

The inner surface of door 74 has, as shown in detail in FIG. 5, pushers 75 consisting of spring plungers to completely push the bolus 32 and the final collimators 34a, 34b and 34c into predetermined position during closure of the door. They are formed, for example, at two positions corresponding with those of grooves they face on right and left sides (see FIG. 3 where four pushers are prepared bilaterally in upper and lower rows to fix a large bolus 32).

On the front surface of door 74, is placed a pop handle 78 which is so constructed as to make a 90° rotation before it is pushed inward which further ensures the fixation of the bolus and the final collimator.

The back panel 76, as shown in detail in FIG. 5, has a limit switch 80 for each groove which detects the complete insertion of the bolus 32 and the final collimators 34a, 34b and 34c.

The front end of the frame 72 (the lowermost end in FIGS. 3–5) has, for example, four linear touch sensors 82a and 82b, so that, when any one of the four touch sensors is activated, the movement of the radiation beam irradiating section 120 can be arrested. Of these touch sensors, two touch sensors 82a which are placed in the same direction along which the radiation beam irradiating section 120 moves, are covered with rubber so as to enhance safety to humans and physical objects, even if they may touch the latter.

Figure 6:
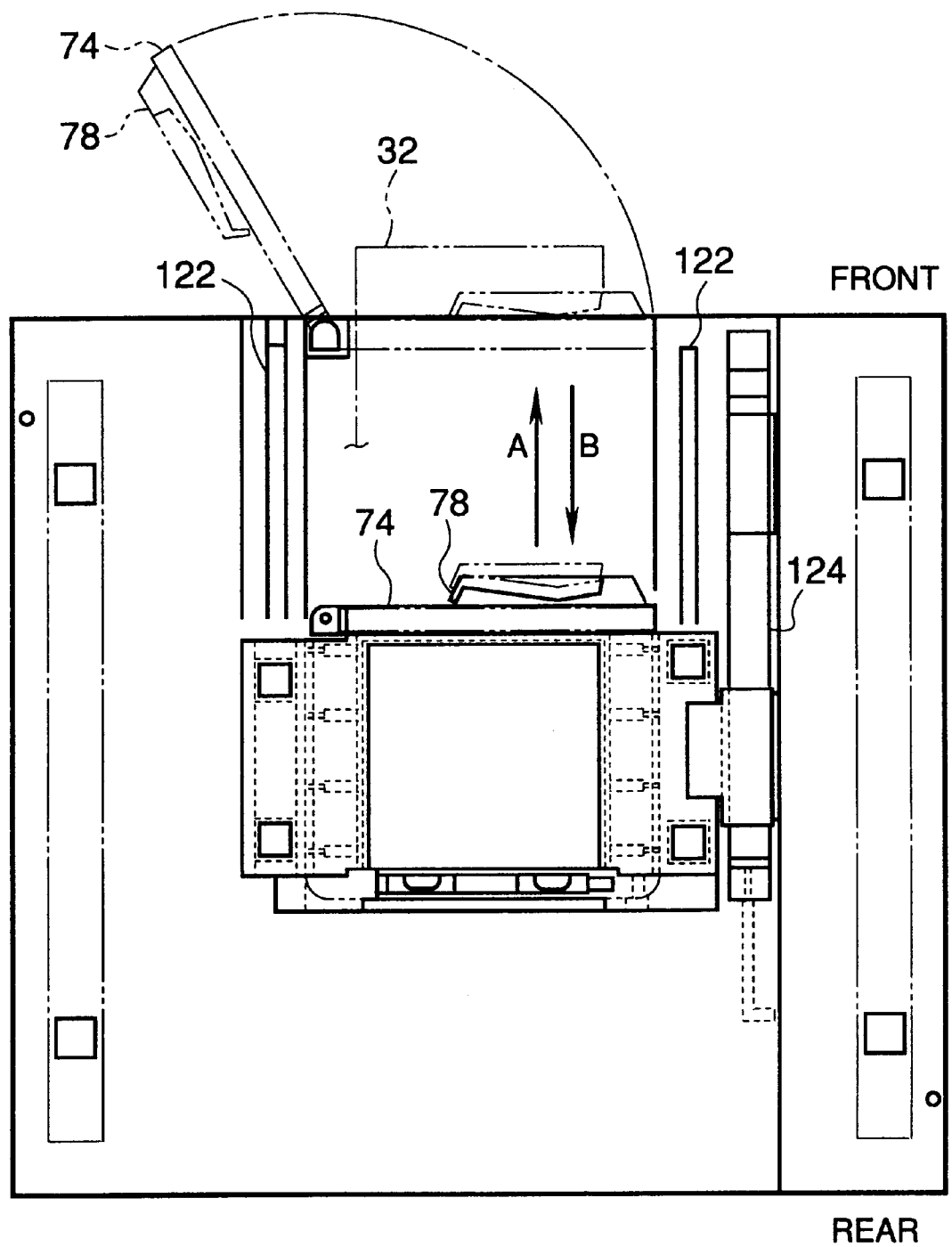
FIG. 6 is a bottom view of the same embodiment.

The frame 72, as shown in detail in FIG. 6, is mounted, for example, on two linear movement (LM) guides 122 bilaterally attached on the bottom surface of the radiation beam irradiating section 120, so that it can move in the anteroposterior direction (vertical direction of FIG. 6) being driven by a rodless cylinder 124 or a sort of air cylinder. It is possible, therefore, whenever exchange of boluses and final collimators is required, to draw out the frame 72 until it reaches the front end (upwards in FIG. 6) of the radiation beam irradiating section 120 as indicated by the arrow A, so that the exchange can be achieved easily.

The operation of the first embodiment will be described below.

Firstly, the rodless cylinder 124 is activated to draw the frame 72 from radiation beam irradiating position at nearly the center of the radiation beam irradiating section 120 up to exchange position of the irradiation field forming members at the front end of the radiation beam irradiating section as shown by the arrow A in FIGS. 5 and 6.

Then, the pop handle 78 is turned to release the door 74, and the bolus and final collimators previously used are drawn out from the frame 72.

Then, a new bolus and final collimators to replace the old ones have the bilateral projected lines 33a and 33b engaged with the grooves 73a and 73b of frame 72 in succession, and the former is inserted into the latter.

On completion of the insertion, the door 74 is closed; the pop handle 78 is turned; and the door 74 is pushed inward. Then, by way of pushers 75 provided on the door 74, the bolus 32 and final collimators 34a, 34b and 34c are pushed until they hit against the back panel 76 of the frame 72.

After it is checked on the basis of output from the limit switch 80 that the bolus 32 and the final collimators 34a, 34b, 34c have been sufficiently pushed inward to reach a specified position, the rodless cylinder 124 is activated, and the frame 72 is returned to the radiation beam irradiating position as indicated by arrow B of FIGS. 5 and 6.

Then, the overall structure of the radiation beam irradiating section 120 is rotated as appropriate round the patient, its position is adjusted and therapy is conducted.

In this embodiment, the back panel 76 is used to determine the accurate positioning of the bolus and the final collimators, but the means for accurate positioning is not limited to the back panel. For example, projections to act as a stopper may be attached to the rear end of the frame 72.

Next, the second embodiment of this invention will be described.

Figure 8:
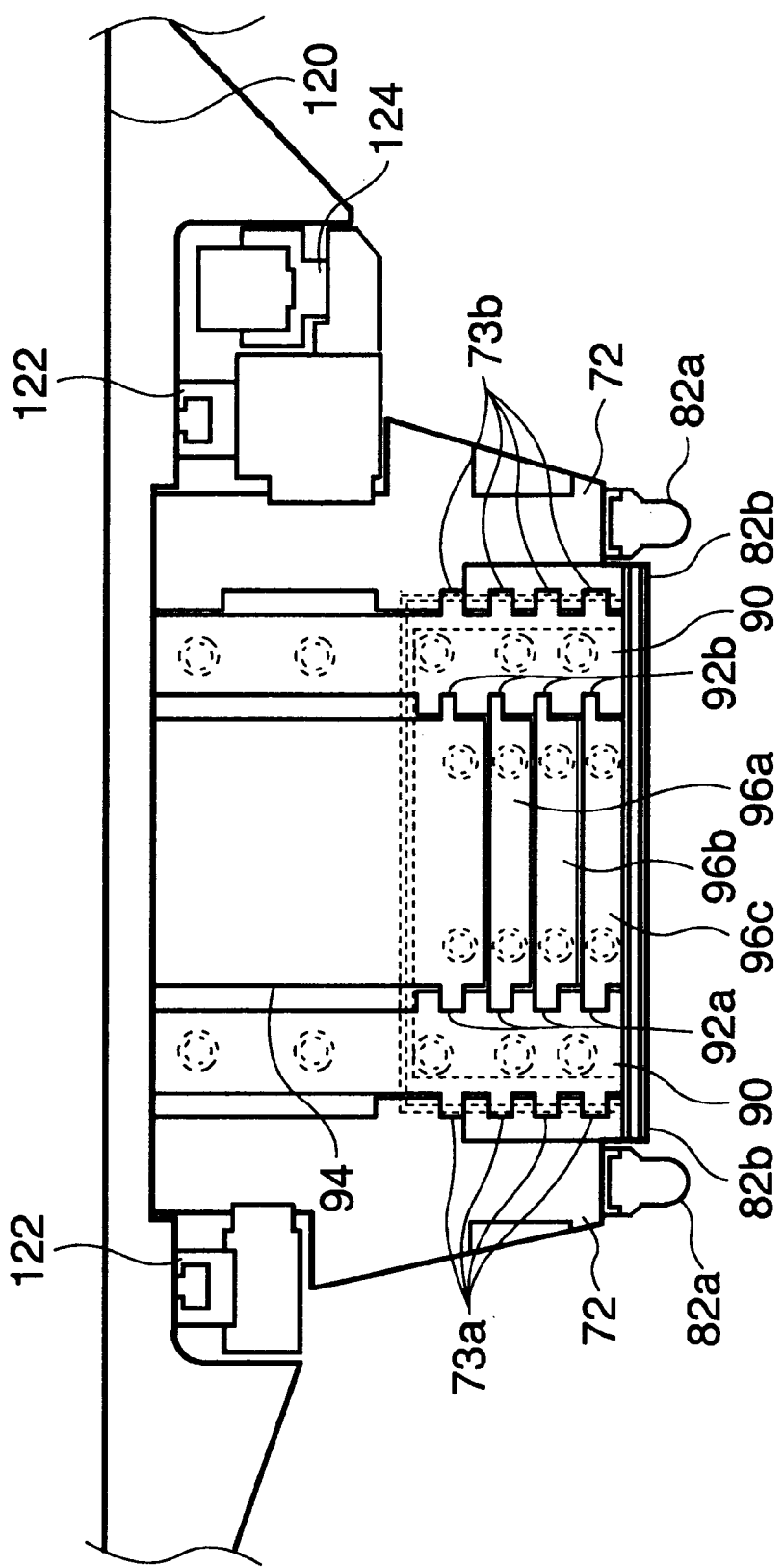
FIG. 8 is a cross-sectional view, viewed from front, illustrating the parts of interest of a second embodiment of this invention.
Figure 9:
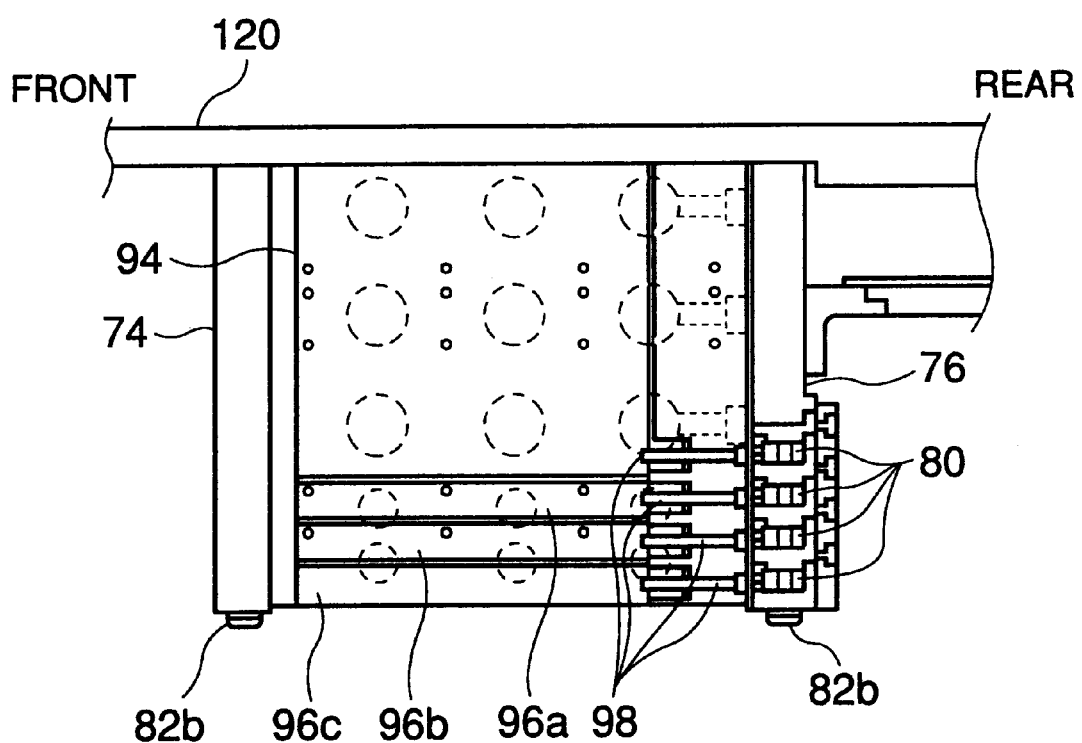
FIG. 9 is a cross-sectional view, viewed from the right side, of the same embodiment.

The second embodiment, as shown in FIGS. 8 and 9, is provided with an adapter 90 which is used for inserting a small bolus 94 and small final collimators 96a, 96b and 96c into the same grooves 73a, 73b, of the same frame 72.

Figure 10:
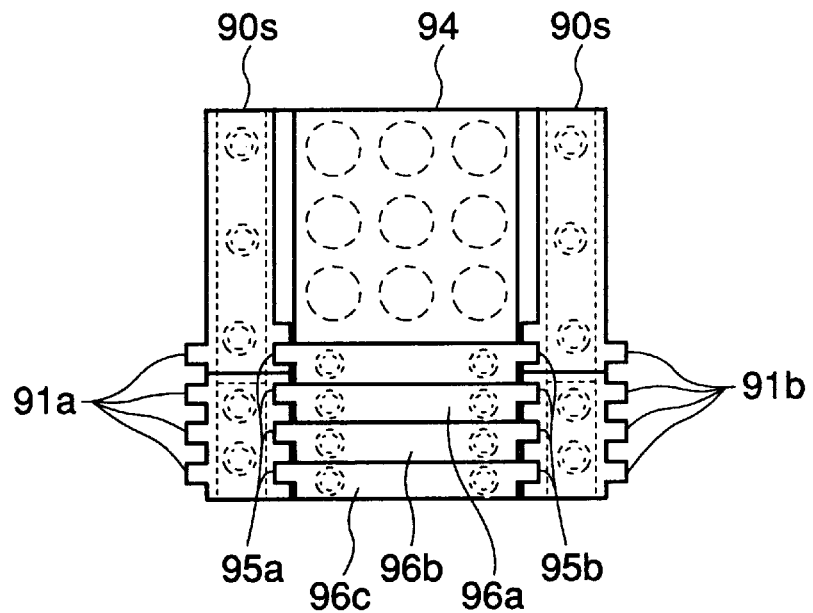
FIG. 10 is a front view of the adapter used in the second embodiment.
Figure 11:
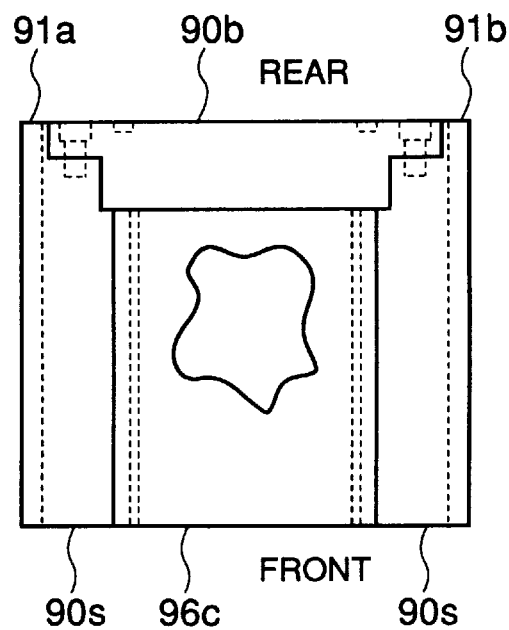
FIG. 11 is a bottom view of the same embodiment.
Figure 12:
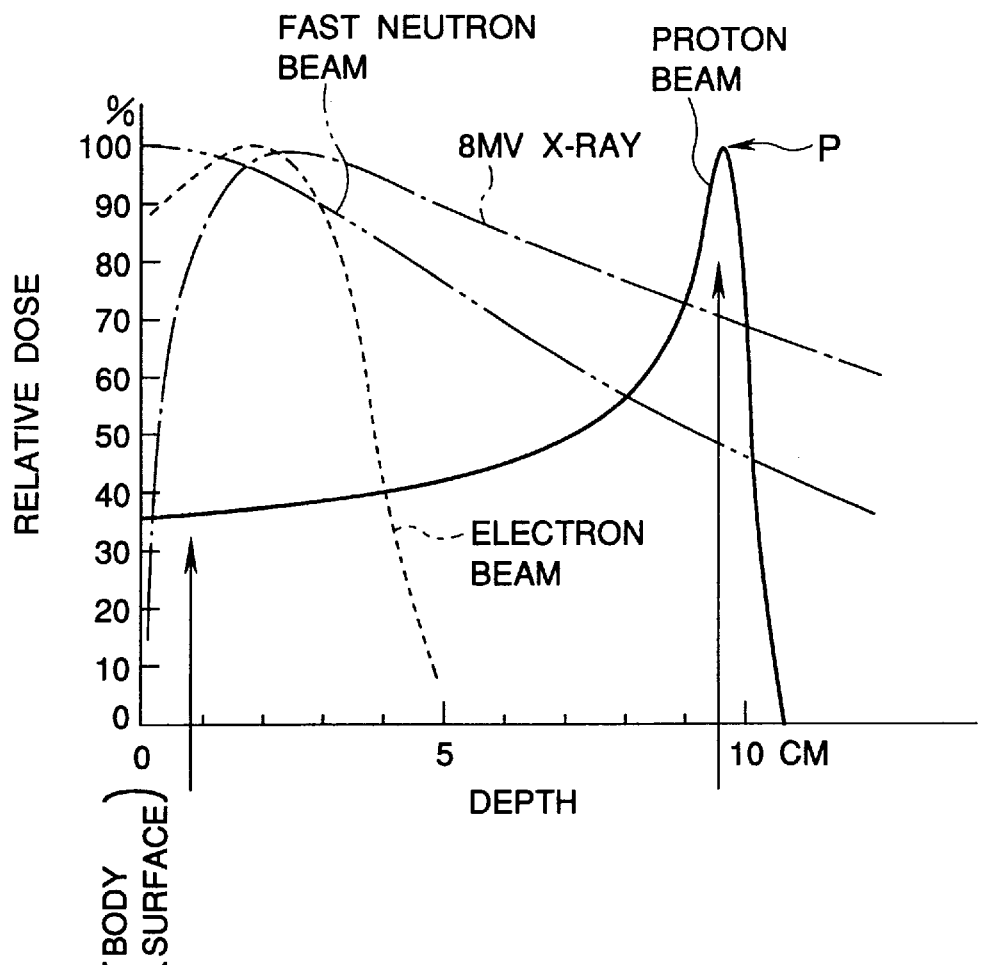
FIG. 12 is graphs illustrating the principle underlying the proton radiation therapy.
Figure 13:
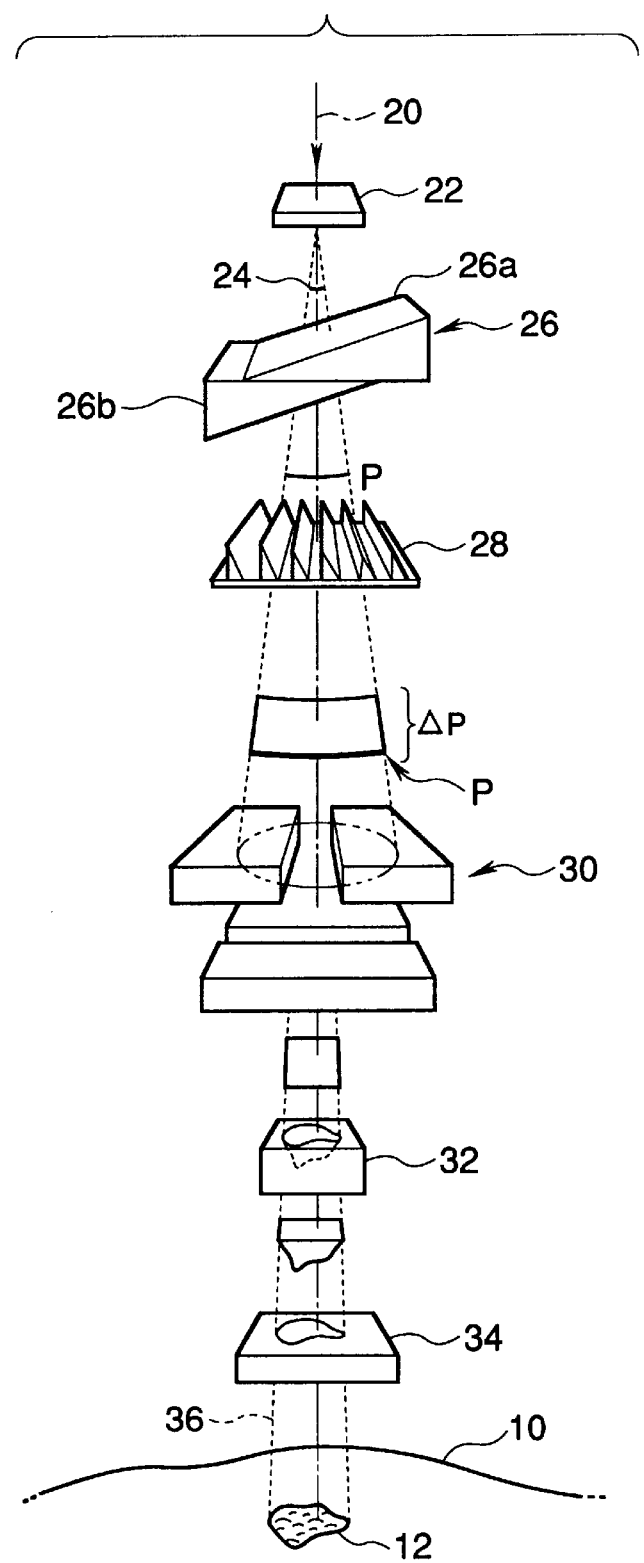
FIG. 13 is a perspective view of elements illustrating the principle of irradiation field formation achieved for the proton radiation therapy.

The adapter 90 has, on the bilateral outer surfaces of its side frame 90s, protruded lines 91a and 91b to engage with the grooves 73a and 73b of the frame 72 as shown in detail in FIGS. 10 and 11. Similarly, the adapter 90 has, on the bilateral inner surfaces of the same side frame 90s, grooves 92a and 92b to engage with the projected lines 95a and 95b of the small bolus 94 and the small final collimators 96a, 96b and 96c. Further, as shown in FIG. 9, the adapter 90 has rods 98 embedded in its back frame 90b which transmit, when the small bolus 94 and the small final collimators 96a, 96b and 96c are pushed inward to contact therewith, the movement to the limit switches 80.

According to this second embodiment, when a lesion to be treated is small, and thus it only requires a small bolus and small final collimators for therapy, firstly the adapter 90 is inserted into the frame 72; and the small bolus 94 and the small final collimators 96a, 96b and 96c are inserted by way of the grooves 92a and 92b of the adapter 90 so that therapy can performed in the same manner as for a lesion of a normal size.

Because such small bolus 94 and small final collimators 96a, 96b and 96c are light in weight as compared with a normal sized bolus 32 and normal sized final collimators 96a, 96b and 96c, they are easy to handle, and finding a place for their storage is also easy.

Although, in above embodiments, the final collimator is divided in three layers in the radiation direction of a proton beam, the division number is not limited to three; it may be divided into two or into four or more. Or, it may be a single unit as with the conventional collimator.

Although, in above embodiments, the present invention is applied to a proton radiation therapy system, what the present invention can be applied to is not limited to this. It may be apparently applied with the same profit to other radiation therapy systems based on the use of X-rays, electron beams and so on.

What is claimed is:

1. An apparatus for fixing a radiation beam irradiation field forming member to form an irradiation field matching with a shape of an object to be irradiated, when radiation beams are irradiated in a gantry, which fixes, to an end of radiation beam irradiating section within the gantry, the irradiation field forming member which comprises a bolus and a final collimator, of which the former adjusts a shape of cross-section of irradiation field at largest depth; and the latter finally determines a shape of the irradiation field, comprising:

a frame fixed on an end of radiation beam irradiating section and having on both sides grooves through which the bolus and the final collimator to be inserted from front;

a door through which the bolus and the final collimator which have been inserted into the frame are pushed from front up to a specified position; and a member which places the bolus and the final collimator thus pushed by way of the door into proper position at rear part of the frame.

2. The apparatus for fixing a radiation beam irradiation field forming member as set forth in claim 1 wherein cross-sections of the grooves provided on both sides of the frame are made asymmetrical, so that the bolus and the final collimator can not be inserted into the frame in reverse manner with respect to anteroposterior direction.

3. The apparatus for fixing a radiation beam irradiation field forming member as set forth in claim 1 wherein the final collimator is divided into plural components in radiation direction of the radiation beams, so that the components are placed one over another to have a laminated structure in the frame for use.

4. The apparatus for fixing a radiation beam irradiation field forming member as set forth in claim 1 wherein the door has, on its inside part, pushers through which the bolus and the final collimator can be perfectly pushed in place when the door is closed.

5. The apparatus for fixing a radiation beam irradiation field forming member as set forth in claim 4 wherein the pushers comprise spring plungers which are mounted on positions corresponding with respective grooves.

6. The apparatus for fixing a radiation beam irradiation field forming member as set forth in claim 4 wherein the door has a pop handle.

7. The apparatus for fixing a radiation beam irradiation field forming member as set forth in claim 1 wherein a limit switch is provided close to rear end of inner surface of the frame to check that the bolus and the final collimator have been perfectly inserted into predetermined position.

8. The apparatus for fixing a radiation beam irradiation field forming member as set forth in claim 1 wherein a touch sensor is provided on front end of the frame so that, when the touch sensor is activated, movement of the radiation beam irradiating section is arrested.

9. The apparatus for fixing a radiation beam irradiation field forming member as set forth in claim 8 wherein the touch sensor comprises a linear touch sensor which is placed so as to surround front end of the radiation beam irradiating section.

10. The apparatus for fixing a radiation beam irradiation field forming member as set forth in claim 9 wherein the touch sensor has, on at least a part thereof, an elastic member attached to moderate impact when the frame hits against something hard.

11. The apparatus for fixing a radiation beam irradiation field forming member as set forth in claim 1 wherein the member to ensure accurate positioning comprises a back panel.

12. The apparatus for fixing a radiation beam irradiation field forming member as set forth in claim 1 wherein the bolus and the final collimator have, on both of their lateral sides, projected lines to engage with the grooves.

13. The apparatus for fixing a radiation beam irradiation field forming member as set forth in claim 1 wherein the bolus and the final collimator have barcodes attached thereupon.

14. The apparatus for fixing a radiation beam irradiation field forming member as set forth in claim 1 wherein the frame is prepared such that it can move in anteroposterior direction and that it can be drawn to a position at front end of the radiation beam irradiating section where the radiation beam irradiation field forming members are exchanged.

15. The apparatus for fixing a radiation beam irradiation field forming member as set forth in claim 1 further comprising an adapter which allows a small bolus and a small final collimator to be used when required size of irradiation field is small, to be inserted into the frame.

16. The apparatus for fixing a radiation beam irradiation field forming member as set forth in claim 15 wherein a rod is embedded in the back frame of the adapter which, when the small bolus and the small final collimator are pushed in, transmits the movement to a limit switch to detect complete insertion of the small bolus and the small final collimator.

* * * * *